United States Patent [19]

Kudo et al.

[11] 3,974,188

[45] Aug. 10, 1976

[54] PROCESS FOR PRODUCING CHOLESTANE TYPE STEROIDS

[75] Inventors: Toshihiro Kudo, Odawara; Moriaki Higo, Hiratsuka; Kazuhiko Suzaki, Odawara; Shiro Tomono, Kanagawa; Masafu Shinbo, Odawara, all of Japan

[73] Assignee: The Lion Dentifrice Co., Ltd., Tokyo, Japan

[22] Filed: Dec. 18, 1974

[21] Appl. No.: 533,834

[30] Foreign Application Priority Data

Jan. 30, 1974  Japan.............................. 49-11760

[52] U.S. Cl.............................. 260/397.2; 424/238
[51] Int. Cl.².......................................... C07C 9/00
[58] Field of Search............................... 260/397.2

[56] References Cited

OTHER PUBLICATIONS

Journal of the Chemical Soc. (1971), Article by Cremlyn et al., pp. 20-23-2027.

Primary Examiner—Elbert L. Roberts
Attorney, Agent, or Firm—Oblon, Fisher, Spivak, McClelland & Maier

[57] ABSTRACT

A process for producing cholestanyl phosphate or epicholestanyl phosphate or salts thereof in which the hydroxyl group at the three-position of cholestanol or epicholestanol is converted into the phosphoric ester by reaction with a phosphorylating agent in an inert solvent and hydrolyzing or hydrogenating this ester.

12 Claims, 1 Drawing Figure

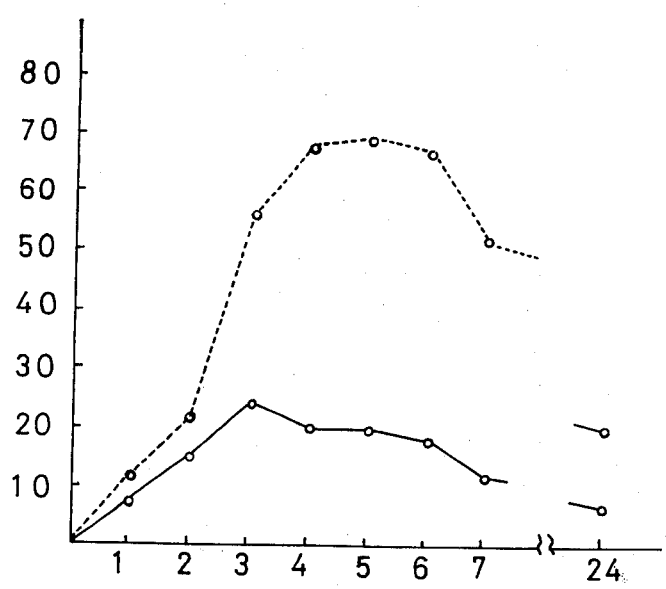

PROCESS FOR PRODUCING CHOLESTANE TYPE STEROIDS

BACKGROUND OF THE INVENTION

1. Field of the Invention

The present invention relates to a process for producing cholestane type steroids.

2. Description of Prior Art

The glucide corticoids, cortisone, and hydrocortisone have been known as hormones secreted from the synnema suprarenal cortex arising from stimulation by ACTH of the frontal lobe of the hypophysis.

Predonisone and predonisolone have been known as synthetic hormones. These hormones have an antiinflammatory effect on affected parts because of their ability to promote absorption from blood capillaries. Accordingly, they are applied for rheumatic affections such as rheumatic arthritis, acute rhumatism fever, and ophthalomologic inflammatory affections.

While these glucide corticoids have high antiinflammatory effect, they also have pronounced side-effects. This, coupled with the fact that they are sparingly soluble in water limits their use in topical application and injection.

SUMMARY OF THE INVENTION

Accordingly, it is one object of the present invention to provide a process for producing cholestane-type steroids such as phosphoric esters of cholestanol, epicholestanol and salts thereof which are water soluble and have excellent antiinflammatory action as well as little side effects.

This and other objects of this invention as will hereinafter become more readily apparent from the following description have been attained by producing cholestanyl phosphate epicholestanyl phosphate or a salt thereof by reacting a phosphorylating agent with cholestanol or epicholestanol so as to esterify the hydroxyl group at the three-position and hydrating or hydrogenating the resulting product.

DETAILED DESCRIPTION OF THE PREFERRED EMBODIMENTS

Exemplary of the salts of phosphoric esters of cholestanol and epicholestanol which can be produced by this invention are the alkali metal salts, e.g., Li, Na, K salts, alkaline earth metal salts, e.g., Ca, Mg, Ba salts, ammonium salts and amine salts.

Epicholestanol has the formula (I) and the cholestanol has the formula (II).

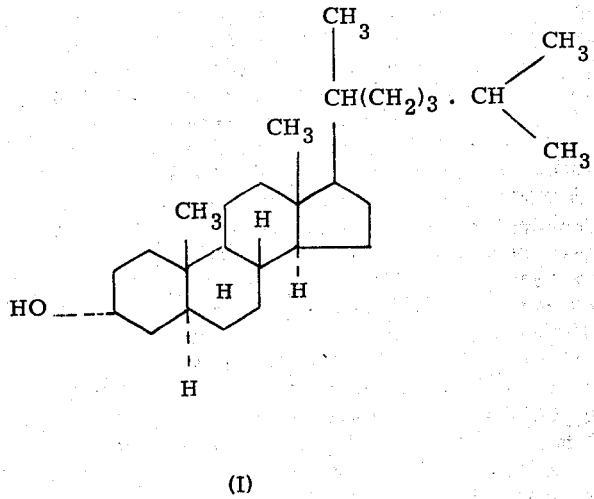

(I)

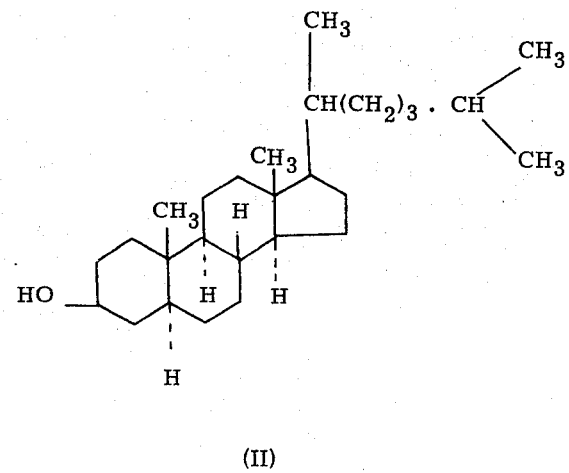

(II)

The hydroxyl group at three-position of formula (I) or (II) is converted to a phosphoric ester by a phosphorylating agent.

The phosphorylating agents used in this invention have the formula

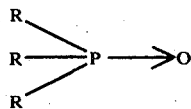

wherein R represents halogen, hydroxyl group, lower alkoxy, haloalkoxyl, cyanoalkoxy, phosphoryloxy

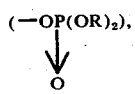

amino, morpholino, imidazolyl, aryloxy such as phenyloxy, halophenyloxy or nitrophenyloxy, or aralkyloxy such as benzyloxy, nitrobenzyloxy or halobenzyloxy, and at least one of R is a halogen, hydroxyl or phosphoryloxy. The typical phosphorylating agents can be phosphoryl trichloride, phosphoryl monochloride, pyrophosphoryl chloride, metaphosphoryl chloride, phenylphosphoryl dichloride, diphenylphosphroyl chloride, nitrophenylphosphoryl dichloride, dibenzylphosphoryl chloride, β-cyanoethyl phosphate, bis (β-cyanoethyl) phosphoryl chloride, bis (β,β,β-trichloroethyl) phosphoryl chloride, morpholinophosphoryl dichloride, dimorpholinophosphoryl chloride, pyrophosphate polyphosphoric acid and tetrakis (p-nitrophenyl) pyrophosphoric acid. It is especially preferable to use phosphoryl trichloride (POCl₃). The reaction product is converted to cholestanyl or epicholestanyl phosphate by hydrolysis with water, an alkaline solution, an acidic solution, an aqueous dioxane solution, an aqueous acetone solution, etc. The concentration of the alkaline solution or the acidic solution is 0.01 N to 20 N preferably 0.1 N to 5 N. The typical reaction is as follows:

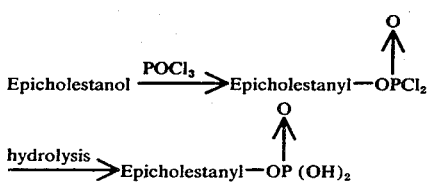

When an arylphosphoryl compound (at least one of R is aryloxy group) or an aralkylphosphoryl compound (at least on of R is aralkyloxy group) is used as the phosphorylating agent, the reaction product can be converted to cholestanyl or epicholestanyl phosphate by hydrogenation as well as by hydrolysis of the reaction product. The hydrogenation can be carried out with hydrogen in the presence of a catalyst especially a palladium or a platinum-type catalyst.

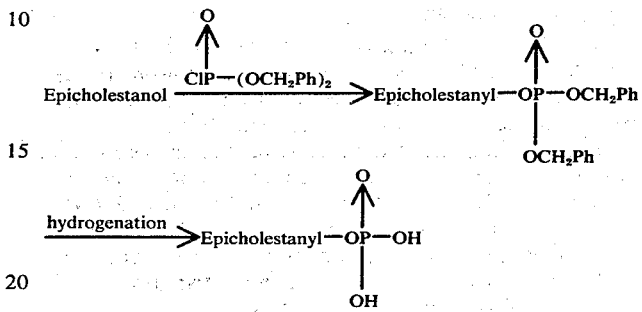

The reaction for converting the hydroxyl group at the three-position of (I) or (II) to a phosphoric ester, can be carried out by reacting phosphoryl trichloride in an inert solvent such as acetone, chloroform, carbon tetrachloride, methylene chloride, ethylene chloride, ether, acetonitrile, dimethylformamide, tetrahydrofuran, benzene or petroleum ether in the presence of a tertiary amine such as pyridine, lutidine, triethylamine, dimethylaniline or an alkali metal hydroxide, alkaline earth metal hydroxide or an alkali metal carbonate or an alkaline earth metal carbonate at relatively low temperature, such as 0°—80°C and hydrolyzing the resulting product by treating it with water or aqueous dioxane, aqueous acetone, etc. The product is neutralized with an alkali, e.g., an alkali metal hydroxide, alkaline earth metal hydroxide, alkali metal carbonate or alkaline earth metal carbonate, and is treated with an ion-exchange resin to give the cholestanyl or epicholestanyl phosphates. If desired, the cholestanyl or epicholestanyl phosphates can be converted to salts by reaction with an alkali metal hydroxide, an alkaline earth metal hydroxide, an alkali metal carbonate, an alkaline earth metal carbonate, ammonia, an amine, etc. These salts can also be obtained by hydrolysis with the corresponding alkaline compound before treatment with the ion-exchange resin. The reaction for converting the hydroxyl group at the three-position of formula (I) or (II) to the corresponding phosphoric ester can be carried out by reacting dibenzylphosphoryl chloride or diphenylphosphoryl chloride in an inert solvent such as chloroform or carbon tetrachloride in the presence of a tertiary amine at a relatively low temperature, such as 0°–80°C and hydrolyzing the resulting dibenzyl compound or diphenyl compound in an acidic or basic solution. Hydrogenation instead of the hydrolysis, can also be used to give the same product. The product is treated with an ion-exchange resin to give the phosphoric acid ester of cholestanol or epicholestanol, or a salt thereof. When a phosphorylating agent having no halogen atom is used, the reaction for converting the hydroxyl group at the three-position of formula (I) or (II) to a phosphoric ester can be carried out by reacting the phosphorylating agent having no halogen atoms (e.g.

β-cyanoethyl phosphate) in the presence of a condensing agent (a condensation-dehydrating agent). Typical condensing agents are dicyclohexylacarbodiimide, trichloroacetonitrile, p-toluenesulfonyl chloride, triisopropylbenzenesulfonyl chloride or the combination 2,2'-dipyridyldisulfide and triphenylphosphine. When the phosphorylation is carried out by using β-cyanoethyl phosphate at room temperature, the product is hydrolyzed with an alkali to remove the cyanoethyl group, whereby the desired products can be obtained. Among the products of this invention, the dipotassium salt of cholestanyl or epicholestanyl phosphates is especially useful as it has superior antiinflammatory effect.

Having generally described the invention, a more complete understanding can be obtained by reference to certain specific examles, which are included for purposes of illustration only and are not intended to be limiting unless otherwise specified.

EXAMPLE 1

The pharmacological test results of the compounds of this invention are as follows.

Acute toxicity:
 $LD_{50}$ (mouse male, 5 weeks)
 1. dipotassium epicholestanyl phosphate
  intraperitoneal    1580 mg/kg
  oral       9300 mg/kg
 2. epicholestanyl phosphate
  intraperitoneal    1850 mg/kg 1. Test for inhibition of sarcomatous growth
(Rat cotton pellet method)*

| Agent | Rat | Weight | Inhibition rate (%) | Dose (mg/kg) |
|---|---|---|---|---|
| None | 9 | 123.2 ± 0.9   135.8 ± 3.7 | — | — |
| $K_2$—PEEC | 7 | 121.4 ± 1.8   129.0 ± 4.9 | 21.5 | 100 |
| EC | 7 | 116.7 ± 0.6   133.9 ± 2.3 | 6.9 | 100 |
| $K_2$—PEC | 7 | 125.6 ± 1.6   123.2 ± 3.4 | 10.0 | 100 |
| C | 7 | 125.4 ± 0.8   144.7 ± 3.8 | 4.5 | 100 |

*Meier, R., Schuler, W. and Desaulees, P. : Experienta, 6, (1950)
Note
$K_2$—PEEC = diptossium epicholestanyl phosphate
EC = epicholestanol
$K_2$—PEC = dipotassium cholestanyl phosphate
C = cholestanol 2. Test for inhibition of edema in the heel of hind leg (Rat)*

The test results showing the rates of edema for the rats are shown in the FIGURE. Note: In the FIGURE, -O-: 100 mg/kg of dipotassium epicholestanyl phosphate, -O-: no dose

* Van Arman, C. G., Begany, A. J., Miller L. M., and Pless, H. H.: J. Pharmacol Exp. Ther., 150, 328 (1965)

3. Test for inhibition of the acceleration of vascular diffusion
(Test for inhibition of cutaneous chromoleaching of rat)**

| Agent*** | Dose mg/kg P.C. | Mean blueing area ($mm^2$ ± S.E.*) | Inhibition rate (%) |
|---|---|---|---|
| None | — | 200 ± 8.0 | — |
| EC | 50 | 191 ± 9 | 4.5 |
|  | 100 | 180 ± 4 | 10 |
| $K_2$—PEEC | 50 | 164 ± 4 | 18 |
|  | 100 | 158 ± 6 | 21 |
| C | 50 | 191 ± 5 | 4.5 |

-continued
3. Test for inhibition of the acceleration of vascular diffusion
(Test for inhibition of cutaneous chromoleaching of rat)**

| Agent*** | Dose mg/kg P.C. | Mean blueing area ($mm^2$ ± S.E.*) | Inhibition rate (%) |
|---|---|---|---|
|  | 100 | 188 ± 3 | 6 |

*standard error
**Juduh, J. D. and Willoughby, D.A.; J. Path. Buct., 83, 567 (1962)
***See table in part 1)

When 100 mg/kg of epicholestanyl phosphate (PEEC) was administered the acceleration of vascular diffusion was inhibited. It is clear that the dipotassium salt of the epicholestanyl phosphate is remarkably effective as an antiinflammatory agent. In the case of acute rhumatism fever, an initial dose of about 50 – 200 mg/day with a maintenance dose of about 10 – 50 mg/day is necessary for an adult human. The application of these compounds to affected parts can also be accomplished by using them in the form of ointments, lotions, creams, powders, and aerosol sprays for the skin; suppositories for the rectum or vagina; germicidal eye-drops, or ointments for the eye or ear; sustained release oral pellets, chewing gum, dentifirce compositions, sprays for the nose, etc. The pharmaceutical compositions for the skin can be in many desirable forms such as hydrophobic ointments, water-soluble ointments and creams, solutions, dispersion or emulsion-type creams and lotions. These compositions are prepared by using a base, a diluent, etc., together with cholestanyl or epicholestanyl phosphate.

EXAMPLE 2

A solution of 10 g of epicholestanol in 150 ml of anyhydrous pyridine was added dropwise to a solution of 14.7 g of phosphoryl trichloride in 80 ml of anhydrous acetone, at −35° – −39°C during 2.5 hours, and the mixture was further stirred at that temperature for 2 hours. After the reaction, 200 ml of water was added to the reaction mixture to decompose the remaining phosphoryl trichloride. Solvent soluble components were extracted by using chloroform and then petroleum ether, and the extract solutions were mixed, concentrated and dried to give 17.0 g of a white powder. The powder was stirred with water for a period of 3 hours. After the reaction, the reaction mixture was cooled and the resulting white suspension centrifugally separated. 11.43 g of white precipitate was isolated and was dissolved in 0.25N — KOH. The solution was treated with a H-type ion-exchange resin, Amberlite IR – 120B, and the resulting solution was concentrated to give the phosphoric acid ester of epicholestanol. The crude product was recrystallized from a mixture of benzene-ethanol, to give 9.5 g of this compound. (melting point of 156° – 160°C).

| Elementary analysis: | | $C_{27}H_{49}O_4P$ | |
|---|---|---|---|
|  |  | C (%) | H (%) |
| Calculated |  | 69.20 | 10.54 |
| Found |  | 68.69 | 10.50 |
| IR spectrum: | 2300 $cm^{-1}$ (P—O—H), | | |
|  | 1220 $cm^{-1}$ (P=O), | | |
|  | 1025 $cm^{-1}$ (P—O—C). | | |
| Mass spectrum: | $M^+$— TMS m/e 612. | | |

EXAMPLE 3

A solution of 3.0 g of cholestanol in 15 ml of anyhydrous pyridine was added dropwise to a solution of 4.4 g of phosphoryl trichloride in 15 ml of acetone at −77°C over 2.5 hours. The mixture was further stirred at −77°C for 1.5 hours. After the reaction, 200 ml of water was added to the reaction mixture giving a white suspension. The precipitate was centrifugally separated and dried under reduced pressure. The resulting white powder was admixed with 75 ml of 90% aqueous dioxane, and the mixture was refluxed for three hours and cooled. The precipitated crystals were filtered and dissolved in 0.35N—KOH. The solution was treated with a H-type ion-exchange resin Amberlite IR–120B, and the resulting solution was concentrated to give cholestanyl phosphate. The crude product was recrystallized from benzene to give 1.5 g of this compound. (melting point of 183° − 184°C).

| Elementary analysis: | $C_{27}H_{49}O_4P$ | |
|---|---|---|
| | C (%) | H (%) |
| Calculated | 69.20 | 10.54 |
| Found | 69.58 | 10.92 |
| IR spectrum: | 2300 cm$^{-1}$ (P—O—H), | |
| | 1230 cm$^{-1}$ (P=O), | |
| | 1010 cm$^{-1}$ (P—O—C). | |

EXAMPLE 4

A solution of 0.70 g of sulfuryl chloride in 3 ml of carbon tetrachloride was added dropwise to a solution of 1.35 g of dibenzyl phosphite in 17 ml of carbon tetrachloride at 17°C in a nitrogen atmosphere while stirring. After the addition, nitrogen gas was bubbled through the mixture and the mixture allowed to react for two hours. The resulting dibenzylphosphoryl chloride was added dropwise to a solution of 1.0 g of cholestanol in a mixture of 10 ml of chloroform and 1 ml of pyridine at −45°C to −40°C while stirring. After the addition, the mixture was kept at this temperature for 2 hours, then allowed to warm to room temperature. After 12 hours, 4 ml of water was added to the reaction mixture over several hours. This mixture was concentrated. The concentrate was then dissolved in 20 ml of a solvent mixture of ethanol and ether (1:1). The pH of the solution was made alkaline by adding 0.1M—Ba(OH)$_2$ and the product extracted with ether several times. The ether solutions were mixed and concentrated to give a pale yellow oil. The oil was dispersed in 60 ml of 95% ethanol and hydrogenated at room temperature at atmospheric pressure in the presence of 0.14 g of palladium oxide. After the reaction, the product was admixed with barium hydroxide to convert it to a barium salt. The barium salt was treated with an H-type ion-exchange resin, Amberlite IR–120B and the product was purified with benzene to give 440 mg of the cholestanyl phosphate. (melting point of 183 − 185°C).

EXAMPLE 5

A solution of 0.70 g of sulfuryl chloride in 3 ml of carbon tetrachloride was added dropwise to a solution of 1.35 g of dibenzyl phosphite in 17 ml of carbon tetrachloride at 17°C in a nitrogen atmosphere while stirring. After the addition, nitrogen gas was bubbled through the mixture. The mixture was allowed to react for 2 hours. The resulting dibenzylphosphoryl chloride was added dropwise to a solution of 1.0 g of epicholestanol in a solvent mixture of 10 ml of chloroform and 1 ml of pyridine at −12°C while stirring. After the reaction, the reaction mixture was kept at room temperature for twelve hours, and 5 ml of water was added. The mixture was then concentrated and the concentrate dissolved in chloroform. The resulting solution was washed with an aqueous solution of sodium bicarbonate and then with water to give a yellow oil. The oil was dispersed in 45 ml of 95% ethanol, and hydrogenated at room temperature at atmospheric pressure in the presence of 0.11 of palladium oxide. After the reaction, the product was admixed with barium hydroxide to convert it to the barium salt. The barium salt was treated with a H-type ion-exchange resin Amberlite IR–120B and the product was concentrated to give 250 mg of the epicholestanyl phosphate. (melting point of 159° − 160°C (recrystallized from a mixture of benzene-ethanol).

EXAMPLE 6

A solution of 0.74 of diphenylphosphoryl chloride in 10 ml of anhydrous pyridine was added dropwise to a solution of 0.97 g of cholestanol in 15 ml of anhydrous pyridine at −20°C while stirring. The mixture was stirred for 1 hour while raising the temperature to 0°C. After 12 hours at this temperature, 10 ml of water was added and the solvent was distilled under reduced pressure to give a white viscous oil. The oil was dissolved in benzene and the solution washed with water and then with 0.1M—K$_2$CO$_3$ and then with water again. The benzene layer was separated, dried over sodium carbonate and concentrated to give colorless crystals of diphenyl cholestanyl phosphate in quanitative yield, melting point of 91.5° − 92.5°C (recrystallized from a mixture of acetone-acetonitrile).

A mixture of 0.93 g of the diphenyl cholestanyl phosphate, 1.89 g of barium hydroxide, 1 ml of n-butanol and 10 ml of water was refluxed for 4.5 hours. After the addition of 5 ml of water, carbon dioxide was bubbled through the solution at about 100°C. The resulting white precipitate was filtered, and 30 ml of 50% acetic acid solution was poured over the precipitate several times. The residue was washed with water and dried to give the barium salt of phenyl cholestanyl phosphate in a yield of 90%. The product was dissolved in 30 ml of 0.1N—H$_2$SO$_4$ and 25 ml of tetrahydrofuran. The mixture was refluxed for 50 minutes and allowed to cool to room temperature. A white precipitate was formed. The precipitate was filtered, the filtrate concentrated and the residue was admixed with water. The water insoluble colorless crystals were filtered, washed with water and dried to give 0.5 g of phenyl cholestanyl phosphate. (melting point of 192° − 194°C [recrystallized from acetic acid]).

In a suspension of 0.11 g of phenyl cholestanyl phosphate and 0.11 g of palladium oxide in 5 ml of acetic acid, 24 ml of hydrogen was introduced at room temperature at atmospheric pressure. The catalyst was filtered and the filtrate was concentrated to give colorless crystals of the cholestanyl phosphate. (melting point of 184° − 185°C [recrystallized from acetic acid]).

EXAMPLE 7

20 ml of anhydrous pyridine was added to 0.78 g of cholestanol and 9.32 g of an 8% pyridine solution of β-cyanoethyl phosphate, and the solvent was stripped off at room temperature under reduced pressure. 40 ml of anhydrous pyridine was added to the residue and the solvent was stripped off in the same manner. The same operation was further repeated to remove water in the reaction system, and 20 ml of anhydrous pyridine was added to give a colorless transparent solution. 2.47 g dicyclohexylcarbodiimide was added to the solution, whereby white crystals were precipitated. The reaction mixture was sealed and stirred at room temperature for 2 hours. 5 ml of water was added to this mixture and the solvent was stripped off under reduced pressure.

The operation was repeated and water was added to the product. White crystals of 1,3-dicyclohexylurea were filtered from the solution. The filtrate was admixed with 40 ml of 1N—NaOH, the mixture refluxed for 40 minutes, and after cooling gave white crystals. The crystals were filtered, washed with water and were dispersed in water. H-type ion-exchange resin Amberlite IR-120B was added to the suspension, the solution was separated from the resin and concentrated. The residue was dried under reduced pressure on $P_2O_5$ to give 0.66 g of the cholestanyl phosphate. (melting point of 182° – 185°C (recrystallized from acetic acid).

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A process for producing cholestanyl phosphate, epicholestanyl phosphate or salts thereof which comprises reacting a phosphorylating agent with a solution of cholestanol or epicholestanol and a tertiary amine in an inert solvent at 0°C – –80°C, whereby the hydroxyl group at the three-position of cholestanol or epicholestanol is converted to the corresponding phosphate ester and hydrolyzing or hydrogenating said phosphate ester.

2. The process according to claim 1, wherein the hydrolyzed product is treated with an ion-exchange resin.

3. The process according to claim 1, wherein the hydrolysis is carried out in an acidic or alkaline aqueous solution by heating under reflux condition.

4. The process according to claim 1, wherein the phosphorylating agent is phosphoryl trichloride, dibenzylphosphoryl chloride, diphenylphosphoryl chloride, or β-cyanoethyl phosphate, and the inert solvent is acetone, chloroform, or carbon tetrachloride.

5. The process according to claim 1, wherein said phosphate ester is neutralized with an alkaline compound.

6. The process according to claim 1, wherein the phosphorylating agent having no halogen atom is used together with a condensation-dehydrating agent.

7. The process according to claim 1, wherein the phosphorylating agent is phosphoryl trichloride and the hydrolysis is performed with an alkaline solution, water, an aqueous acetone solution or an aqueous dioxane solution.

8. Epicholestanyl phosphate and salts thereof.

9. A method for suppressing inflammation in the body which comprises administering an effective amount for suppressing inflammation of epicholestanyl phosphate and salts thereof.

10. A method for suppressing inflammation in the body which comprises administering an effective amount for suppressing inflammation of dipotassium epicholestanyl phosphate.

11. The phosphate of claim 8 which is an alkali metal or an alkaline earth metal salt.

12. The phosphate of claim 11 which is dipotassium epicholestanyl phosphate.

* * * * *